United States Patent [19]

Keller et al.

[11] Patent Number: 4,843,069

[45] Date of Patent: Jun. 27, 1989

[54] MEDICAMENT FORMULATIONS CONTAINING RUTHENIUM COMPOUNDS WITH AN ANTITUMORAL ACTION

[75] Inventors: Heimo Keller; Bernhard Keppler, both of Heidelberg, Fed. Rep. of Germany

[73] Assignee: Asta Pharma AG, Fed. Rep. of Germany

[21] Appl. No.: 849,455

[22] PCT Filed: Jul. 24, 1985

[86] PCT No.: PCT/EP85/00369

§ 371 Date: Mar. 21, 1986

§ 102(e) Date: Mar. 21, 1986

[87] PCT Pub. No.: WO86/00905

PCT Pub. Date: Feb. 13, 1986

[30] Foreign Application Priority Data

Jul. 24, 1984 [CH] Switzerland ...................... 03594/84
Jul. 4, 1985 [CH] Switzerland ...................... 02907/85

[51] Int. Cl.$^4$ .................. A61K 31/40; A61K 31/435; C07F 4/00

[52] U.S. Cl. .................................... 514/184; 514/188; 544/179; 544/181; 544/225; 546/4; 548/103

[58] Field of Search ...................... 544/179, 181, 225; 548/103; 514/184, 188, 185, 186, 187

[56] References Cited

U.S. PATENT DOCUMENTS 4,549,018  10/1985  Siedle .................................. 544/225

Primary Examiner—Mary C. Lee
Assistant Examiner—J Richter
Attorney, Agent, or Firm—Berman, Aisenberg & Platt

[57] ABSTRACT

A compound of the general formula I

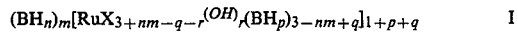

$$(BH_n)_m[RuX_{3+nm-q-r}(OH)_r(BH_p)_{3-nm+q}]_{1+p+q} \quad I$$

wherein
B denotes a mononuclear or polynuclear basic heterocyclic radical containing one or more nitrogen atoms,
X denotes chlorine or bromine,
m denotes 1 or 2,
n denotes 1 or 2, the sum of n and m being not greater than 3,
p denotes 0 or 1, but not 1 if n is 1,
q denotes 0 or 1, but not 1 if p is 1 and
r denotes 0 or 1, show an antitumoral activity and are therefore suitable as a chemotherapeutic for the treatment of cancers.

18 Claims, No Drawings

MEDICAMENT FORMULATIONS CONTAINING RUTHENIUM COMPOUNDS WITH AN ANTITUMORAL ACTION

TECHNICAL FIELD

The invention relates to medicament formulations containing ruthenium compounds with an antitumoral action, and methods for the treatment of cancers.

PRIOR ART

Of the compounds of the platinum metals, the complex compound cis-diamminedichloroplatinum (II) has proved to be a potent antitumoral agent. An inhibition of tumor growth has also been observed with compounds of the other platinum metals in studies with animal experiments (for example T. Giraldi et al., Cancer Res. 37 [1977] 2662-6). An antitumoral action of ruthenium red is reported by L. J. Anghileri (Z. Krebsforsch. 83 [1975] 213-7). The potential suitability of ruthenium complexes for cancer therapy is discussed by M. J. Clarke, ACS Symp. Ser. 140 [1980] 157–180. The synthesis of complex compounds of trivalent ruthenium with pyrazole and imidazole is described by F. Kralik et al, Collection Czechoslov. Chem. Commun. 26 [1961] 1298.

DESCRIPTION OF THE INVENTION

It has been found that the complex compounds of the general formula I

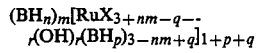   I wherein
- B denotes a mononuclear or polynuclear unsaturated basic heterocyclic radical containing one or more ring nitrogen atoms,
- X denotes chlorine or bromine,
- m denotes 1 or 2,
- n denotes 1 or 2, the sum of n and m being not greater than 3,
- p denotes 0 or 1, but not 1 if n is 1,
- q denotes 0 or 1, but not 1 if p is 1 and
- r denotes 0 or 1, have an advantageous antitumoral activity coupled with favorable toxicity. They are therefore suitable as chemotherapeutics for the treatment of cancers. As chemotherapeutic agents with few side effects, they are suitable for the treatment of tumors, for example ovarian tumors, mammary tumors, stomach tumors, prostate tumors, lung tumors, bladder tumors and, in particular, colorectal tumors, and other malignant neoplasms. The compounds are accordingly useful for alleviating pain and suffering associated with cancer therapy, for inhibition and regression of tumors and for alleviating symptoms and increasing life expectancy.

The invention therefore relates to medicament formulations containing these ruthenium complex compounds, and use of the complex compounds for preparation of medicament formulations, in particular those useful for treating cancers, and methods for the treatment of organisms suffering from cancer.

Particularly preferred medicament formulations are those containing complex compounds of the general formula I'

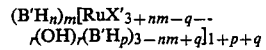   I' wherein
- B' denotes pyridine, pyrimidine, pyridazine or triazine, which can be substituted by hydroxyl, amino, halogen, $C_2$-$C_4$-alkyl, $C_2$-$C_4$-alkenyl, $C_1$-$C_4$-alkylmercapto, formyl, $C_1$-$C_4$-alkoxycarbonyl, $C_1$-$C_4$-alkoxycarbonyl-$C_1$-$C_4$-alkylene, di-$C_1$-$C_4$-alkylamino, di-$C_1$-$C_4$-alkylamine-$C_1$-$C_4$-alkylene, di-$C_1$-$C_4$-alkylaminocarbonyl, di-$C_1$-$C_4$-alkylaminocarbonyl-$C_1$-$C_4$-alkylene, hydroxyiminomethine, phenyl, benzyl, benzoyl, pyrrolidino, piperidino, pyrrol-1-yl or pyrrol-1-yl-$C_1$-$C_4$-alkylene, or denotes a ring

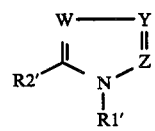

wherein
- R1' denotes hydrogen, sodium, $C_1$-$C_4$-alkyl or phenyl and
- R2' denotes hydrogen, $C_1$-$C_4$-alkyl, amino or phenyl, or R1' and R2' together denote a group —$(CH_2)_s$—, wherein s represents an integer from 4 to 8,
- W denotes nitrogen or CR3', wherein R3' denotes hydrogen, $C_1$-$C_4$-alkyl, amino or phenyl, preferably hydrogen or methyl,
- Y denotes nitrogen or CR4', wherein R4' denotes hydrogen, $C_1$-$C_4$-alkyl, amino or phenyl, preferably hydrogen or methyl, and
- Z denotes nitrogen or CR5', wherein R5' denotes hydrogen, $C_1$-$C_4$-alkyl, amino or phenyl, preferably hydrogen or methyl, but at least one of the radicals R3', R4' or R5' denotes hydrogen,
- or denotes purine, adenine, guanine or cytosine, and
- X' denotes chlorine or bromine and
- m, n, p, q and r have the above meanings.

Particularly preferred medicament formulations are those containing complex compounds of the general formula I"

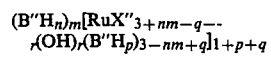   I"

wherein
- B" denotes pyridine, which can be substituted, preferably in the 4-position, by hydroxyl, amino, chlorine, diethylamino, dimethylamino, hydroxyiminomethine, phenyl, pyrrolidino, piperidino or pyrrol-1-ylmethyl, or denotes pyrrole, imidazole, 1-methylimidazole, 4-methylimidazole, pyrazole, 4-methylpyrazole, triazole, 1-sodium pyrazole, 1-phenyltetrazole, 5-phenyltetrazole, adenine, guanine, purine or cytosine and
- x" denotes chlorine and
- m, n, p, q and r have the above meanings.

Especially preferred medicament formulations are those containing imidazolium diimidazoletetrachlororuthenate(III), bisimidazolium imidazolepentachlororuthenate(III), bispyrazolium pyrazolehydroxotetrachlororuthenate(III), and/or bis(4-methylpyrazolium) (4-methylpyrazole)hydroxotetrachlororuthenate(III).

The compounds of the general formula Ia

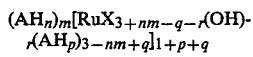

wherein
A denotes a mononuclear or polynuclear basic heterocyclic radical which contains one or more nitrogen atoms, with the exception of pyrazole and imidazole, and
X denotes chlorine or bromine, and
m, n, p, q and r have the above meanings,
are novel and the invention therefore furthermore relates to these.

Preferred compounds are those of the general formula Ia'

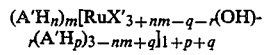

wherein
A' denotes pyridine, pyrimidine, pyridazine or triazine, which can be substituted by hydroxyl, amino, halogen, $C_1$-$C_4$-alkyl, $C_2$-$C_4$-alkenyl, $C_1$-$C_4$-alkylmercapto, formyl, $C_1$-$C_4$-alkoxycarbonyl, $C_1$-$C_4$-alkoxycarbonyl-$C_1$-$C_4$-alkylene, di-$C_1$-$C_4$-alkylamino, di-$C_1$-$C_4$-alkylamine-$C_1$-$C_4$-alkylene, di-$C_1$-$C_4$-alkylamino-carbonyl, di-$C_1$-$C_4$-alkylamino-carbonyl-$C_1$-$C_4$-alkylene, hydroxyiminomethine, phenyl, benzyl, benzoyl, pyrrolidino, piperidino, pyrrol-1-yl or pyrrol-1-yl-$C_1$-$C_4$-alkylene, or denotes a ring

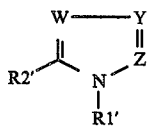

wherein
R1' denotes hydrogen, sodium, $C_1$-$C_4$-alkyl or phenyl and
R2' denotes hydrogen, $C_1$-$C_4$-alkyl, amino or phenyl, or R1' and R2' together denote a group —(CH$_2$)$_s$—, wherein s represents an integer from 4 to 8,
W denotes nitrogen or CR3', wherein R3' denotes hydrogen, $C_1$-$C_4$-alkyl, amino or phenyl, preferably hydrogen or methyl,
Y denotes nitrogen or CR4', wherein R4' denotes hydrogen, $C_1$-$C_4$-alkyl, amino or phenyl, preferably hydrogen or methyl, and
Z denotes nitrogen or CR5', wherein R5' denotes hydrogen, $C_1$-$C_4$-alkyl, amino or phenyl, preferably hydrogen or methyl, but at least one of the radicals R3', R4' or R5' denotes hydrogen,
or denotes purine, adenine, guanine or cytosine, but not pyrazole or imidazole, and
X' denotes chlorine or bromine and
m, n, p, q and r have the above meanings.

Particularly preferred compounds are those of the general formula Ia''

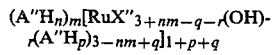

wherein
A'' denotes pyridine, which can be substituted, preferably in the 4-position, by hydroxyl, amino, chlorine, diethylamino, dimethylamino, hydroxyiminomethine, phenyl, pyrrolidino, piperidino or pyrrol-1-ylmethyl, or denotes pyrrole, 1-methylimidazole, 4-methylimidazole, 4-methylpyrazole, triazole, 1-sodiumpyrazole, 1-phenyltetrazole, 5-phenyltetrazole, adenine, guanine, purine or cytosine and
X'' denotes chlorine and
m, n, p, q and r have the above meanings.

Overall, 5-membered heterocyclic radicals are preferred over 6-membered and over polynuclear radicals for A, A', A'', B, B' and B'' in the general formulae I, I', I'', Ia, Ia' and Ia''.

The ruthenium complex compounds are prepared by the procedure described by F. Kralik et al., Collection Czechoslov. Chem. Commun. 26 [1961] 1298. The nitrogen-heterocyclic compounds are added to a solution of ruthenium(III) chloride or bromide. The desired product separates out or is precipitated by addition of an organic solvent or by concentrating the reaction solution and/or cooling. An example of a suitable solvent for the ruthenium(III) halide is a mixture of ethanol and aqueous hydrogen halide acid. The ruthenium-(III) halide is preferably dissolved in a 1:1 mixture of ethanol and 1N aqueous hydrogen halide acid. It is advantageous to boil this solution under reflux for about 4 to 16, preferably about 12, hours and then to concentrate it to approximately one quarter of the volume. The basic heterocyclic compounds are advantageously added to the ruthenium(III) halide solution as a solution in aqueous acid, preferably hydrogen halide acid. For example, the heterocyclic compounds are added as a solution in 6N aqueous hydrogen halide acid. The reaction mixture is left at room temperature or heated under reflux for about half an hour to three hours. The heterocyclic compounds are known or can be prepared by methods which are known per se.

The invention furthermore relates to a process for the preparation of the compounds of the general formula Ia, Ia' or Ia'', wherein A, A' or A'', X, X' or X'' and m, n, p, q and r have the abovementioned meanings, which comprises reacting a ruthenium(III) halide of the formula RuX$_3$, RuX'$_3$ or RuX''$_3$, wherein X, X' and X'' have the abovementioned meanings, with the nitrogen-heterocyclic compound AH, A'H, or A''H of the abovementioned meaning.

The process according to the invention is preferably carried out in a hydrogen halide acid medium, in particular a mixture of a lower alkanol, especially ethanol, with aqueous hydrogen halide acid.

$C_1$-$C_4$-Alkyl is straight-chain or branched, preferably straight-chain. $C_1$-$C_4$-Alkylene is straight-chain or branched, for example methylene, ethylene, propylene, trimethylene or tetramethylene, straight-chain radicals being preferred.

The medicament formulations according to the invention are administered, above all, intravenously, but also intramuscularly, intraperitoneally, subcutaneously or perorally. External administration is also possible. Administration by intravenous injection or intravenous infusion is preferred.

The medicament formulations are prepared by processes which are known per se, the compounds according to the invention being used as such or, if appropriate, in combination with suitable pharmaceutical excipients. If the novel pharmaceutical formulations contain pharmaceutical excipients in addition to the active compound, the active compound content of these mixtures is 0.1 to 99.5, preferably 0.5 to 95, per cent by weight of the total mixture.

In accordance with the invention, an active compound is used in any suitable formulation, provided that the development or maintenance of sufficient levels of active compound is guaranteed. This can be achieved, for example, by oral or parenteral administration in suitable doses. The pharmaceutical formulation of the active compound is advantageously in the form of unit doses appropriate for the desired administration. A unit dose can be, for example, a tablet, a coated tablet, a capsule, a suppository or a measured volume of a powder, a granular material, a solution, an emulsion or a suspension.

"Unit dose" in the context of the present invention is understood as a physically discrete unit which contains an individual amount of the active ingredient in combination with a pharmaceutical excipient, the content of active compound in the unit dose corresponding to a fraction or multiple of a therapeutic individual dose. An individual dose preferably contains the amount of active compound which is given in one administration and usually corresponds to a whole or one half, one third or one quarter of a daily dose. If only a fraction, such as one half or one quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention can contain about 0.1 to 500 mg, advantageously 10 to 200 mg and in particular 50 to 150 mg, of active compound.

In general, in human medicine, the active compound or compounds are administered in a daily dose of 0.1 to 5, preferably 1 to 3, mg/kg of body weight, in the case of oral administration, if appropriate in the form of several, preferably 1 to 3, individual doses, to achieve the desired results. An individual dose contains the active compound or compounds in amounts of 0.1 to 5, preferably 1 to 3, mg/kg of body weight. Similar dosages can be used for oral treatment.

Therapeutic administration of the pharmaceutical formulation can take place 1 to 4 times daily at specified or varying points in time, for example in each case before meals and/or in the evening. However, it may be necessary to deviate from the dosages mentioned, and in particular to do so in accordance with the nature, body weight and age of the individual to be treated, the nature and severity of the illness, the nature of the formulation and of the administration of the medicament formulation and the time or interval over which administration takes place. Thus, in some cases it may be sufficient to manage with less than the abovementioned amount of active compound, whilst in other cases the abovementioned amount of active compound must be exceeded. It may also be advantageous to administer the medicament formulations only once or at an interval of several days.

The particular optimum dosage and mode of administration of the active compounds required can be determined by any expert on the basis of his expert knowledge.

The pharmaceutical formulations as a rule consist of the active compounds according to the invention and non-toxic, pharmaceutically acceptable medicament excipients, which are used as an admixture or diluent in solid, semi-solid or liquid form or as a means of encasing, for example in the form of a capsule, a tablet coating, a sachet or some other container for the therapeutically active constituent. An excipient can serve, for example, as a promoter for absorption of the medicament by the body, as a formulation auxiliary, as a sweetener, as a flavor correctant, as a colorant or as a preservative.

Examples of forms which may be used orally are tablets, coated tablets, hard and soft capsules, for example of gelatin, dispersible powders, granules, aqueous and oily suspensions, emulsions, solutions or syrups.

Tablets may contain inert diluents, for example calcium carbonate, calcium phosphate, sodium phosphate or lactose; granulating and dispersing agents, for example maize starch or alginates; binders, for example starch, gelatin or gum acacia; and lubricants, for example aluminum stearate, magnesium stearate, talc or silicone oil. They may additionally be provided with a coating, which can also be such that it effects delayed dissolution and absorption of the medicament formulations in the gastro-intestinal tract, so that, for example, a better tolerance, a protracted effect or a retarded effect is achieved. Gelatin capsules can contain the medicament mixed with a solid diluent, for example calcium carbonate or kaolin, or an oily diluent, for example olive oil, peanut oil or paraffin oil.

Aqueous suspensions, which, if appropriate, are prepared at short notice, may contain suspending agents, for example sodium carboxymethylcellulose, methylcellulose, hydroxypropylcellulose, sodium alginate, polyvinylpyrrolidone, gum tragacanth or gum acacia; dispersing and wetting agents, for example polyoxyethylene stearate, heptadecaethyleneoxy cetanol, polyoxyethylene sorbitol monooleate, polyoxyethylene sorbitan monooleate or lecithin; preservatives, for example methyl or propyl hydroxybenzoates; flavoring agents; and sweeteners, for example sucrose, lactose, sodium cyclamate, dextrose or invert sugar syrup.

Oily suspensions may contain, for example, peanut oil, olive oil, sesame oil, coconut oil or paraffin oil, and thickeners, such as, for example, beeswax, hard paraffin or cetyl alcohol; and furthermore sweeteners, flavoring agents and antioxidants.

Water-dispersible powders and granules may contain a ruthenium complex compound mixed with dispersing, wetting and suspending agents, for example those mentioned above, as well as with sweeteners, flavoring agents and colorants.

Emulsions may contain, for example, olive oil, groundnut oil or paraffin oil, in addition to emulsifying agents, such as, for example, gum acacia, gum tragacanth, phosphatides, sorbitan monooleate or polyoxyethylene sorbitan monooleate, and sweeteners and flavoring agents.

For parenteral use of the medicaments, aqueous suspensions, isotonic salt solutions or other solutions which contain dispersing or wetting agents and/or pharmacologically acceptable diluents, for example propylene glycol or butylene glycol, and/or solubilizing agents, for example TWEEN®s (polysorbates), CREMOPHOR®s (dispersing agents for pharmaceutical purposes) or polyvinylpyrrolidone, are used, these forms being injectable under sterile conditions and, if appropriate, prepared at short notice.

The active compounds can also be employed in the form of coprecipitates with hydrophilic polymers. Coprecipitates can be prepared by mixing solutions of the complex compounds in an anhydrous organic solvent with solutions of hydrophilic polymers, such as, for example, polyvinylpyrrolidone (PVP) or polyoxyethylene sorbitan fatty acid esters (TWEEN ®) or, in particular, glycerolpolyethylene glycol ricinoleate (CREMOPHOR ®EL). The residues which remain after stripping off the solvent or solvents are administered as aqueous solutions. Examples of possible organic solvents are chloroform and methylene chloride, which are rendered anhydrous in the customary manner before being used. It has proved advantageous to use the hydrophilic polymers in a 5- to 50-fold, preferably 10- to 35-fold, excess by weight over the complex compound. It is also possible to introduce the polymers as such into solutions of the complex compounds. The residue which remains after stripping off the solvent or solvents is advantageously freed as far as possible from solvent residues under a high vacuum. Depending on the nature and amount of the hydrophilic polymer used, solid crystalline or vitreous, or liquid or tacky residues are obtained. The latter can as a rule be converted into solid, usually waxy products by cooling. The dissolving properties of the coprecipitates are favorably influenced if dispersing or wetting agents, such as propylene glycol or butylene glycol, preferably propylene glycol, are added to the mixture of the solutions of the complex compound and the hydrophilic polymers during preparation of the coprecipitates.

The active compounds can also be formulated in microencapsulated form, if appropriate with one or more of the excipients or additives mentioned.

The following examples illustrate the invention in more detail, without limiting it.

Preparation Examples

1. General Instructions 10 g (38.3 mmol) of ruthenium(III) chloride trihydrate are dissolved in a mixture of 250 ml of ethanol and 250 ml of aqueous 1N hydrochloric acid. The solution is boiled under reflux for 12 hours and then concentrated to a volume of 125 ml. This solution contains 0.3 mmol of ruthenium per ml and is called "ruthenium solution" below.

Hydrochloric acid solutions of the basic nitrogen-heterocyclic compound are added to the solution.

2. Detailed Instructions

2.1. Di(1,2,4-triazolium) pentachloro(1,2,4-triazole)ruthenate(III)

$(C_2H_4N_3)_2[RuCl_5(C_2H_3N_3)]$ 0.93 g of 1,2,4-triazole, dissolved in 7.2 ml of 6N hydrochloric acid, are added to 8.9 ml of the ruthenium solution. The mixture is concentrated to two-thirds of the original volume on a rotary evaporator and cooled to 4° C. After 12 hours, a brown precipitate is filtered off.

Melting point: >300° C.
Yield: 0.55 g (50% of theory).
Analysis: calculated: 14.76%, C; 2.25%, H; 25.84%, N. found: 14.45%, C; 2.54%, H; 25.15%, N.

2.2. 1,2,4-Triazolium tetrachlorodi(1,2,4-triazole)ruthenate(III)

$(C_2H_4N_3)[RuCl_4(C_2H_3N_3)_2]$ 5.8 g of 1,2,4-triazole, dissolved in 16.6 ml of 6N hydrochloric acid, are added to 19.7 ml of the ruthenium solution. The mixture is then stirred at room temperature for one hour and the volume of the solution is subsequently reduced to half. A dark brown precipitate thereby begins to form and, after cooling to 4° C., the product can be filtered off with suction.

Melting point: 179° C.
Yield: 1.5 g (56.3% of theory).
Analysis: calculated: 15.97%, C; 2.23%, H; 27.95%, N. found: 16.92%, C; 2.81%, H; 28.66%, N.

2.3. Adeninium di[adeninepentachlororuthenate(III)] tetrahydrate

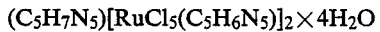
$(C_5H_7N_5)[RuCl_5(C_5H_6N_5)]_2 \times 4H_2O$ 1.5 g (11 mmol) of adenine are dissolved in 100 ml of 4N hydrochloric acid, and 10 ml of the prepared ruthenium solution are added. The mixture is concentrated somewhat on a rotary evaporator and the solution is placed in a refrigerator. After 12 hours, a brown precipitate can be filtered off with suction.

Melting point: >300° C.
Yield: 0.8 g (51.6% of theory).
Analysis: calculated: 17.35%, C; 2.62%, H; 20.23%, N. found: 17.81%, C; 2.75%, H; 20.29%, N.

2.4. Guaninium pentachloroguanineruthenate(III) dihydrate

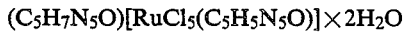
$(C_5H_7N_5O)[RuCl_5(C_5H_5N_5O)] \times 2H_2O$ 3 g (19.8 mmol) of guanine are dissolved in 100 ml of hot 4N hydrochloric acid and the solution is added dropwise to 7.5 ml of the ruthenium solution. The mixture is boiled under reflux for one hour and the coffee-brown precipitate is then filtered off hot, with suction.

Melting point: >300° C.
Yield: 0.78 g (56.1% of theory).
Analysis: calculated: 19.41%, C; 2.61%, H; 22.64%, N. found: 19.92%, C; 2.57%, H; 22.57%, N.

2.5. Dicytosiniumpentachlorocytosineruthenate(III) pentahydrate

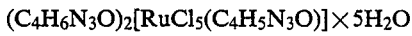
$(C_4H_6N_3O)_2[RuCl_5(C_4H_5N_3O)] \times 5H_2O$ 1 g (9 mmol) of cytosine is dissolved in 50 ml of hot 4N hydrochloric acid and 3 ml of the ruthenium solution are added. After one night in a refrigerator, a red-brown precipitate separates out and, after filtering off with suction, is dried under a high vacuum.

Melting point: 190°-195° C.
Yield: 0.21 (41.2% of theory)
Analysis: calculated: 20.46%, C; 3.83%, H; 17.90%, N. found: 21.52%, C; 3.17%, H; 18.29%, N.

2.6. Purinium purinepentachlororuthenate(III)

$(C_5H_6N_4)[RuCl_5(C_5H_4N_4)]$ 1.4 g (11.7 mmol) of purine are dissolved in 3 ml of 6N hydrochloric acid. 4 ml of the ruthenium solution are added to the solution. A coffee-brown precipitate is obtained.

Melting point: >300° C.
Yield: 0.39 g (62.4% of theory).
Analysis: calculated: 23.07%, C; 1.94%, H; 21.53%, N. found: 23.91%, C; 2.07%, H; 22.27%, N.

2.7. Bis(1-methylimidazolium) pentachloro-1-methylimidazoleruthenate(III)

$(C_4H_7N_2)_2[RuCl_5(C_4H_6N_2)]$ 2 g (24 mmol) of 1-methylimidazole are dissolved in 4 ml of 6N hydrochloric acid and the solution is added to 10 ml of the ruthenium solution. The product is precipitated by addition of ethanol.
Melting point: 150°–153° C. (discoloration at 75° C.).
Yield: 1.2 g (75.9% of theory).
Analysis: calculated: 27.36%, C; 4.21%, H. found: 27.50%, C; 4.01%, H.

2.8. Bis[1-sodium-(1,2,4-triazolium)] pentachloro[1-sodium-(1,2,4-triazole]ruthenate(III)

$(C_2H_3N_3Na)_2[RuCl_5(C_2H_2N_3Na)_2]$ 2.67 g of 1-sodium-(1,2,4-triazole) are dissolved in 5 ml of water, 0.5 ml of 6N hydrochloric acid is added, and 10 ml of the ruthenium solution are added. When left to stand for 12 hours, red-brown crystals precipitate.
Melting point: 120° C.
Yield: 1.2 g (71.9% of theory).
Analysis: calculated: 13.94%, C; 1.45%, H; 22.65%, N. found: 12.50%, C; 2.26%, H; 21.68%, N.

2.9. 4-Methylimidazolium tetrachlorobis(4-methylimidazole)ruthenate(III)

$(C_4H_7N_2)[RuCl_4(C_4H_6N_2)_2]$ 1.21 g (14.7 mmol) of 4-methylimidazole are dissolved in 0.6 ml of 6N hydrochloric acid, and 5 ml of the ruthenium solution are added. The mixture is then concentrated to approximately two-thirds of the original volume and the solution is placed in a refrigerator overnight. After 12 hours, the product has precipitated in the form of dark red crystals. It is filtered off with suction and washed with diethyl ether.
Melting point: 223° C. (substance starts to become viscous at 181° C.).
Yield: 0.49 g (66.6% of theory).
Analysis: calculated: 29.34%, C; 3.90%, H; 17.14%, N. found: 29.44%, C; 4.07%, H; 17.19%, N.

2.10. 1,5-Dimethyltetrazolium bis[pentachloro-1,5-dimethyltetrazoliumruthenate(III)] hydrate $(C_3H_8N_4)[RuCl_5(C_3H_7N_4)]_2 \times H_2O$ 1.44 g of 1,5-dimethyltetrazole are dissolved in a little water and 0.5 ml of 6N hydrochloric acid, and 5 ml of the ruthenium solution are added. The volume is then concentrated to about two-thirds of the original volume and the concentrate is cooled to 4° C. in a refrigerator. After 12 hours, the yellow product can be filtered off with suction.
Melting point: >280° C.
Yield: 0.51 g (71% of theory).
Analysis: calculated: 16.55%, C; 3.49%, H; 25.75%, N. found: 16.23%, C; 2.81%, H; 25.22%, N.

Pharmacology

A. P 388 Leukemia model

About $2 \times 10^5$ or about $10^6$ P 388 leukemia cells in 0.2 ml of physiological saline solution are transferred intraperitoneally (i.p.) to female BDF$_1$ mice about 4 weeks old and weighing 18 to 20 g. The leukemia is kept in passage on DBA/2 mice. The leukemia cells are taken from freshly sacrificed animals immediately before the transplantation. The animals are randomized on transinoculation. 3 to 6 mice are used per dosage. The number of control groups (untreated animals) in more extensive experiments is chosen so that it approximately corresponds to the square of the total number of groups. The substances are injected intraperitoneally, for the first time 24 hours after the transplantation, as aqueous solutions, if necessary with the aid of solubilizing agents, for example TWEEN ® (polyoxyethylene derivatives of sorbitan esters). The experimental conditions correspond to the P 388 leukemia model of the USA National Cancer Institute (NCI). (Methods of Development of New Anticancer Drugs, NCI Monography 45, US Department of Health, Education and Welfare, Public Health Service, March 1977, page 147).

2. Leukemia 1210 model

The experiment is carried out analogously to the P 388 leukemia model described under A.1. $10^5$ L 1210 leukemia cells are transferred. As with the model of the NCI, the substance is administered only once (NCI Monography 45, page 147).

3. Melanoma B16 model

The experiment is carried out analogously to the P 388 leukemia model described under A.1 by the procedure described in NCI Monography 45, page 148. The tumor is transferred subcutaneously (s.c.) as a homogenate (0.5 ml of the homogenate described in the NCI Monography). Therapy takes place on days 1 to 9. The tumor weight is determined on day 22.

4. AMMN-induced autochthonous carcinoma of the colon

The method is described by J. Wagner et al., J. Cancer Res. Clin. Oncol. 104 [1985] 115–131. The colon tumor is induced in male Sprague-Dawley rats by ten intrarectal administrations of 2 mg/kg/week of N-nitrosoacetoxymethyl-methylamine (AMMN). After the ten-week induction period, the tumor is allowed to grow for five weeks. This is followed by the ten-week therapy phase with administration of the test substances twice weekly. The animals are sacrificed and the tumor volume determined one week after the end of therapy.

B. Experimental results

The results of the tumor models described under point A.1, 2. and 3. are summarized in the following table. The dose stated was administered on the days listed in the third column of the table. The factor T/C stated in percent denotes the percentage lengthening of the median survival time of the treated animals in comparison with the median survival time of the untreated control animals.

The experiment is discontinued as soon as the median survival time T/C of the treated animals has reached 300% of the median survival time of the untreated animals. To calculate the median survival time, the animals still living at the end of the experiment are counted as having died at the end of the experiment.

The compounds investigated are characterized by a serial number (Ser. No.):

1 = Bisimidazolium imidazolepentachlororuthenate(III)
2 = Imidazolium diimidazoletetrachlororuthenate(III)
3 = Bispyrazolium pyrazolehydroxotetrachlororuthenate(III)
4 = Bis(4-methylpyrazolium) (4-methylpyrazole)hydroxotetrachlororuthenate(III)
5 = Bis(4-methylimidazolium) (4-methylimidazole)pentachlororuthenate(III)
6 = 2-Methylimidazolium (2-methylimidazole)tetrachlororuthenate(III)
7 = Bis(2-methylimidazolium) (2-methylimidazole)pentachlororuthenate(III)
8 = Di(1,2,4-triazolium) pentachloro(1,2,4-triazole)ruthenate(III)
9 = Purinium purinepentachlororuthenate(III)

10=Dicytosinium pentachlorocytosineruthenate(III) pentahydrate
11=Bis(1-methylimidazolium) (1-methylimidazole)pentachlororuthenate(III)
12=Bis-pyrimidinium pentachloropyrimidineruthenate(III)
13=Adeninium di[adeninepentachlororuthenate(III)] tetrahydrate
14=4-Methylimidazolium tetrachlorobis(4-methylimidazole)ruthenate(III)
15=1,2,4-Triazolium tetrachlorobis(1,2,4-triazole)ruthenate(III)

| Compound Ser. No. | Number of Leukemia cells | Days on which therapy is carried out | Dose [mg/kg] | T/C [%] P388 | L1210 |
|---|---|---|---|---|---|
| Fluorouracil | $10^6$ | 1, 5, 9 | 60 | 131 | |
| 1 | $10^6$ | 1 | 78 | 125 | |
|   | $10^6$ | 1 to 9 | 39 | 170 | |
|   | $10^5$ | 1 | 78 | | 131 |
|   | $10^6$ | 1, 5, 9 | 39 | 200 | |
| 2 | $10^6$ | 1 | 72 | 181 | |
|   | $10^6$ | 1 to 9 | 8 | 181 | |
|   | $2 \times 10^5$ | 1, 5, 9 | 36 | 186 | |
| 3 | $10^6$ | 1 | 75 | 149 | |
|   | $10^6$ | 1 to 9 | 8 | 173 | |
|   | $2 \times 10^5$ | 1, 5, 9 | 28 | 142 | |
| 4 | $10^6$ | 1, 5, 9 | 10 | 180 | |
| 5 | $10^6$ | 1, 5, 9 | 48.9 | 149 | |
| 6 | $10^6$ | 1, 5, 9 | 48.9 | 127 | |
| 7 | $10^6$ | 1, 5, 9 | 48.9 | 138 | |
| 8 | $10^6$ | 1, 5, 9 | 45.1 | 161 | |
|   | $10^6$ | 1, 5, 9 | 83.3 | >250 | |
| 9 | $10^6$ | 1, 5, 9 | 52.1 | 135 | |
| 10 | $10^6$ | 1, 5, 9 | 104.3 | 147 | |
| 11 | $10^6$ | 1, 5, 9 | 52.4 | 120 | |
| 12 | $10^6$ | 1, 5, 9 | 52.0 | 143 | |
| 13 | $10^6$ | 1, 5, 9 | 103.7 | 141 | |
| 14 | $10^6$ | 1, 5, 9 | 48.9 | 120 | |
| 15 | $10^6$ | 1, 5, 9 | 45.1 | 161 | |

Evaluation of the results from the melanoma B16 model showed that the compound with Serial Number 1 had an effect on the animals which received therapy to the extent that their tumor weight was only 10% of the tumor weights of the control animals.

Evaluation of the results from the AMMN-induced autochthonous carcinoma of the colon model showed that the compound with Serial Number 1 (dosage per administration: 12 mg/kg) had an effect on the animals which received therapy to the extent that their tumor volumes were only 20% of the tumor volumes of the untreated control animals. This is all the more surprising since the conventional cytostatics used in clinical treatment, such as, for example, Endoxan or cisplatin, show no therapeutic action on this model under the conditions described. Since this model is regarded as being particularly decisive in respect of the efficacy of compounds tested in the treatment of colon tumors and colorectal tumors in humans, it can be assumed with great probability that the medicament formulations according to the invention are of benefit in the treatment of colon tumors and colorectal tumors in humans.

We claim:

1. A pharmacologically-acceptable complex compound of formula Ia

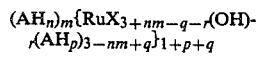

wherein

A denotes an optionally-substituted mononuclear or polynuclear unsaturated heterocyclic radical having no hetero ring member other than a nitrogen atom, each unsaturated ring of which has 5 or 6 ring members, no more than 4 of which are nitrogen atoms, with the exception of pyrazole and imidazole, X denotes chlorine or bromine, m denotes 1 or 2, n denotes 1 or 2, the sum of n and m being not greater than 3, p denotes 0 or 1, but not 1 if n is 1, q denotes 0 or 1, but not 1 if p is 1 and r denotes 0 or 1.

2. A complex compound of claim 1 of the formula Ia'

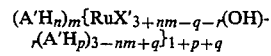

wherein

A' denotes pyridine, pyrimidine, pyridazine or triazine, optionally substituted by hydroxyl, amino, halogen, $C_1$–$C_4$-alkyl, $C_2$–$C_4$-alkenyl, $C_1$–$C_4$-alkylmercapto, formyl, $C_1$–$C_4$-alkoxycarbonyl, $C_1$–$C_4$-alkoxycarbonyl-$C_1$–$C_4$-alkylene, di-$C_1$–$C_4$-alkylamino, di-$C_1$–$C_4$-alkylamine-$C_1$–$C_4$-alkylene, di-$C_1$–$C_4$-alkylaminocarbonyl, di-$C_1$–$C_4$-alkylaminocarbonyl-$C_1$–$C_4$-alkylene, hydroxyiminomethine, phenyl, benzyl, benzoyl, pyrrolidino, piperidino, pyrrol-1-yl or pyrrol-1-yl-$C_1$–$C_4$-alkylene, or denotes a ring

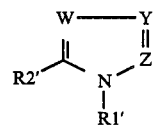

wherein

R1' denotes hydrogen, sodium, $C_1$–$C_4$-alkyl or phenyl and

R2' denotes hydrogen, $C_1$–$C_4$-alkyl, amino or phenyl, or R1' and R2' together denote a group —$(CH_2)_s$—, wherein s represents an integer from 4 to 8, W denotes nitrogen or CR3', wherein R3' denotes hydrogen, $C_1$–$C_4$-alkyl, amino or phenyl, preferably hydrogen or methyl, Y denotes nitrogen or CR4', wherein R4' denotes hydrogen, $C_1$–$C_4$-alkyl, amino or phenyl, preferably hydrogen or methyl, and Z denotes nitrogen or CR5', wherein R5' denotes hydrogen, $C_1$–$C_4$-alkyl, amino or phenyl, preferably hydrogen or methyl, but at least one of the radicals R3', R4' or R5' denotes hydrogen, or denotes purine, adenine, guanine or cytosine, but not pyrazole or imidazole, and X' denotes chlorine or bromine and m, n, p, q and r have the meanings given in claim 1.

3. A complex compound of claim 1 of formula Ia"

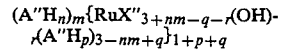

wherein

A″ denotes pyridine, which is optionally substituted, preferably in the 4-position, by hydroxyl, amino, chlorine, diethylamino, dimethylamino, hydroxyiminomethine, phenyl, pyrrolidino, piperidino or pyrrol-1-ylmethyl, or denotes pyrrole, 1-methylimidazole, 4-methylimidazole, 4-methylpyrazole, triazole, 1-sodiumpyrazole, 1-phenyltetrazole, 5-phenyltetrazole, adenine, guanine, purine or cytosine and X″ denotes chlorine and m, n, p, q and r have the meanings given in claim 1.

4. A medicament formulation useful for alleviating pain and suffering associated with cancer therapy and containing pharmaceutically-acceptable excipient and an effective amount of one or more pharmacologically-acceptable complex compounds of formula I $$(BH_n)_m\{RuX_{3+nm-q-r}(OH)_r(BH_p)_{3-nm+q}\}_{1+p+q} \qquad I$$

wherein

B denotes an optionally-substituted mononuclear or polynuclear unsaturated basic heterocyclic radical having no hetero member other than a nitrogen atom, each unsaturated ring of which has 5 or 6 ring members, and no more than 4 of which are nitrogen atoms, X denotes chlorine or bromine, m denotes 1 or 2, n denotes 1 or 2, the sum of n and m being not greater than 3, p denotes 0 or 1, but not 1 if n is 1, q denotes 0 or 1, but not 1 if p is 1 and r denotes 0 or 1.

5. A medicament formulation of claim 4 wherein the unsaturated heterocyclic radical of B comprises a 5-membered unsaturated heterocyclic ring.

6. A medicament formulation of claim 4 wherein the unsaturated heterocyclic radical of B is mononuclear.

7. A medicament formulation of claim 4 in sterile aqueous solution form.

8. In compounding a medicament formulation suitable for treating patients afflicted with cancer and having an active ingredient useful for alleviating pain and suffering associated with cancer therapy, the improvement wherein the active ingredient comprises one or more pharmacologically-acceptable complex compounds of formula I $$(BH_n)_m\{RuX_{3+nm-q-r}(OH)_r(BH_p)_{3-nm+q}\}_{1+p+q} \qquad I$$

wherein

B denotes an optionally-substituted mononuclear or polynuclear unsaturated basic heterocyclic radical having from 1 to 4 nitrogen atoms as the sole ring hetero atoms, and each unsaturated ring of which has 5 or 6 ring members, X denotes chlorine or bromine, m denotes 1 or 2, n denotes 1 or 2, the sum of n and m being not greater than 3, p denotes 0 or 1, but not 1 if n is 1, q denotes 0 or 1, but not 1 if p is 1 and r denotes 0 or 1.

9. A medicament formulation containing pharmaceutically-acceptable excipient and an effective amount of a complex compound of claim 1 (a) to alleviate pain and suffering associated with cancer therapy, (b) for inhibition and regression of tumors, (c) for alleviating cancer symptoms or (d) any combination of the foregoing of a patient to whom the formulation is administered.

10. A medicament formulation of claim 9 in sterile aqueous solution form.

11. A method of compounding of claim 8 wherein the heterocyclic radical of B is neither that of pyrazole nor that of imidazole.

12. A method of treating cancer patients, which comprises administration of an amount of a medicament formulation as claimed in claim 4 which is sufficient to ease the pain and suffering associated with cancer therapy.

13. A method of treating cancer patients with colorectal tumors, which comprises administration of an amount of a medicament formulation of claim 4 containing bisimidazolium imidazolepentachlororuthenate(III), which is sufficient to prevent the further spread of the colorectal tumor and neoplasms.

14. A medicament formulation of claim 4 including a pharmaceutically acceptable excipient and from 0.1 to 99.5 per cent by weight of at least one of the complex compounds of formula I.

15. A method of claim 12 wherein the heterocyclic radical of B is neither that of pyrazole nor that of imidazole.

16. A medicament formulation of claim 4 containing one or more complex compounds of the formula I′

$$(B'H_n)_m\{RuX'_{3+nm-q-r}(OH)_r(B'H_p)_{3-nm+q}\}_{1+p+q} \qquad I'$$

wherein

B′ denotes pyridine, pyrimidine, pyridazine or triazine, which is optionally substituted by hydroxyl, amino, halogen, $C_1$–$C_4$-alkyl, $C_2$–$C_4$-alkenyl, $C_1$–$C_4$-alkyl-mercapto, formyl, $C_1$–$C_4$-alkoxycarbonyl, $C_1$–$C_4$-alkoxycarbonyl-$C_1$–$C_4$-alkylene, di-$C_1$–$C_4$-alkylamino, di-$C_1$–$C_4$-alkylamine-$C_1$–$C_4$-alkylene, di-$C_1$–$C_4$-alkylaminocarbonyl, di-$C_1$–$C_4$-alkylaminocarbonyl-$C_1$–$C_4$-alkylene, hydroxyiminomethine, phenyl, benzyl, benzoyl, pyrrolidino, piperidino, pyrrol-1-yl or pyrrol-1-yl-$C_1$–$C_4$-alkylene, or denotes a ring $$\begin{array}{c} W\!=\!\!=\!\!Y \\ R2'\diagup\diagdown N \diagdown Z \\ \phantom{R2'\diagup\diagdown}| \\ \phantom{R2'\diagup\diagdown}R1' \end{array}$$

wherein

R1′ denotes hydrogen, sodium, $C_1$–$C_4$-alkyl or phenyl and

R2′ denotes hydrogen, $C_1$–$C_4$-alkyl, amino or phenyl, or R1′ and R2′ together denote a group —(CH$_2$)$_s$—, wherein s represents an integer from 4 to 8, W denotes nitrogen or CR3′, wherein R3′ denotes hydrogen, $C_1$–$C_4$-alkyl, amino or phenyl, preferably hydrogen or methyl, Y denotes nitrogen or CR4′, wherein R4′ denotes hydrogen, $C_1$–$C_4$-alkyl, amino or phenyl, preferably hydrogen or methyl, and Z denotes nitrogen or CR5′, wherein R5′ denotes hydrogen, $C_1$–$C_4$-alkyl, amino or phenyl, preferably hydrogen or methyl, but at least one of the radicals R3', R4' or R5' denotes hydrogen, or denotes purine, adenine, guanine or cytosine, and X' denotes chlorine or bromine and m, n, p, q and r have the meanings given in claim 1.

17. A medicament formulation of claim 4 containing one or more complex compounds of the formula I''

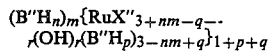

wherein

B'' denotes pyridine, which is optionally substituted, preferably in the 4-position, by hydroxyl, amino, chlorine, diethylamino, dimethylamino, hydroxyiminomethine, phenyl, pyrrolidino, piperidino or pyrrol-1-ylmethyl, or denotes pyrrole, imidazole, 1-methylimidazole, 4-methylimidazole, pyrazole, 4-methylpyrazole, triazole, 1-sodium pyrazole, 1-phenyltetrazole, 5-phenyltetrazole, adenine, guanine, purine or cytosine and x'' denotes chlorine and m, n, p, q and r have the meanings given in claim 1.

18. A medicament formulation of claim 4 containing bisimidazolium imidazolepentachlororuthenate(III), imidazolium diimidazoletetrachlororuthenate(III), bispyrazolium pyrazolehydroxotetrachlororuthenate(III) or bis(4-methylpyrazolium) (4-methylpyrazole)hydroxotetrachlororuthenate(III).

* * * * *